United States Patent [19]

Shlisky

[11] Patent Number: 5,531,341
[45] Date of Patent: Jul. 2, 1996

[54] AUTOCLAVABLE CAP FOR A HAZARDOUS MATERIAL CONTAINER

[76] Inventor: Brian Shlisky, 48 Knight La., Kings Park, N.Y. 11754

[21] Appl. No.: 372,358

[22] Filed: Jan. 13, 1995

[51] Int. Cl.$^6$ ............................................. B65D 51/16
[52] U.S. Cl. ........................ 215/308; 215/261; 215/310; 215/DIG. 3; 215/347; 206/366
[58] Field of Search ................................. 215/261, 308, 215/310, DIG. 3, 274, 347; 220/908; 206/366

[56] References Cited

U.S. PATENT DOCUMENTS

| | | | |
|---|---|---|---|
| 3,315,831 | 4/1967 | Scott | 215/261 |
| 3,326,401 | 6/1967 | De Long | 215/261 X |
| 3,696,958 | 10/1972 | Lee | 215/261 |
| 4,520,926 | 6/1985 | Nelson | 206/366 |
| 5,145,063 | 9/1992 | Lee | 206/364 |
| 5,395,006 | 3/1995 | Verma | 220/371 |

FOREIGN PATENT DOCUMENTS 1174332   8/1985   U.S.S.R. ............................. 215/261

*Primary Examiner*—Stephen K. Cronin

[57] ABSTRACT

A cap for a storage jar or the like for hospital use in storing syringe needles preparatory to disposal, in the construction of which alternating discs of steam permeable construction material and non-needle puncturable construction material, the latter with steam passageway openings, are embodied in the cap so that the syringe needles can be steam autoclaved through the cap, moving through the steam permeable discs and the steam passageway openings of the other discs, so as to sterilize the stored syringe needles, and the steam passageway openings are held out of register or alignment with each other so as to prevent projection of any stored syringe needle out of the jar and coming into contact with a hospital employee or other individual.

2 Claims, 2 Drawing Sheets

5,531,341

AUTOCLAVABLE CAP FOR A HAZARDOUS MATERIAL CONTAINER

The present invention relates generally to storage, preparatory to disposal, of hazardous medical waste, e.g. used syringe needles, and more particularly to steam autoclave treatment of the stored contents while containing safeguards against contact which could result in transmittal of virus infections or other such serious consequence.

EXAMPLE OF THE PRIOR ART

It is already known, as exemplified by U.S. Pat. No. 3,326,401 for "Closure" issued to A. R. DeLong on Jun. 20, 1967, that stored infectious material can be steam autoclaved, and thus sterilized, without removal from the storage container. The closure or bottle cap of the DeLong container for steam autoclaving purposes uses a single disc each of steam permeable construction material and of rigid material, and is provided with aligned openings in these discs for passage of the steam into the container to allow the sterilizing treatment to occur. This safe unrestricted access into the storage compartment provided for the steam unavoidably renders unsafe the handling of the container if the contents is sharp pointed needles or the like which inadvertently could protect in an opposite direction through the provided access and thus out of the storage compartment.

Broadly, it is an object of the present invention to provide a safe syringe needle storage container amenable to steam autoclaving, overcoming the foregoing and other shortcomings of the More particularly, it is an object to embody the within container closure cap with plural discs of steam permeable construction material for steam input, and of puncture-proof construction material discs to safeguard against external projection of the needles, using a cooperative arrangement for these discs that achieves both requirements of steam autoclaving and safe handling, all as will be better understood as the description proceeds.

The description of the invention which follows, together with the accompanying drawings should not be construed as limiting the invention to the example shown and described, because those skilled in the art to which this invention appertains will be able to devise other forms thereof within the ambit of the appended claims.

Figure 1:
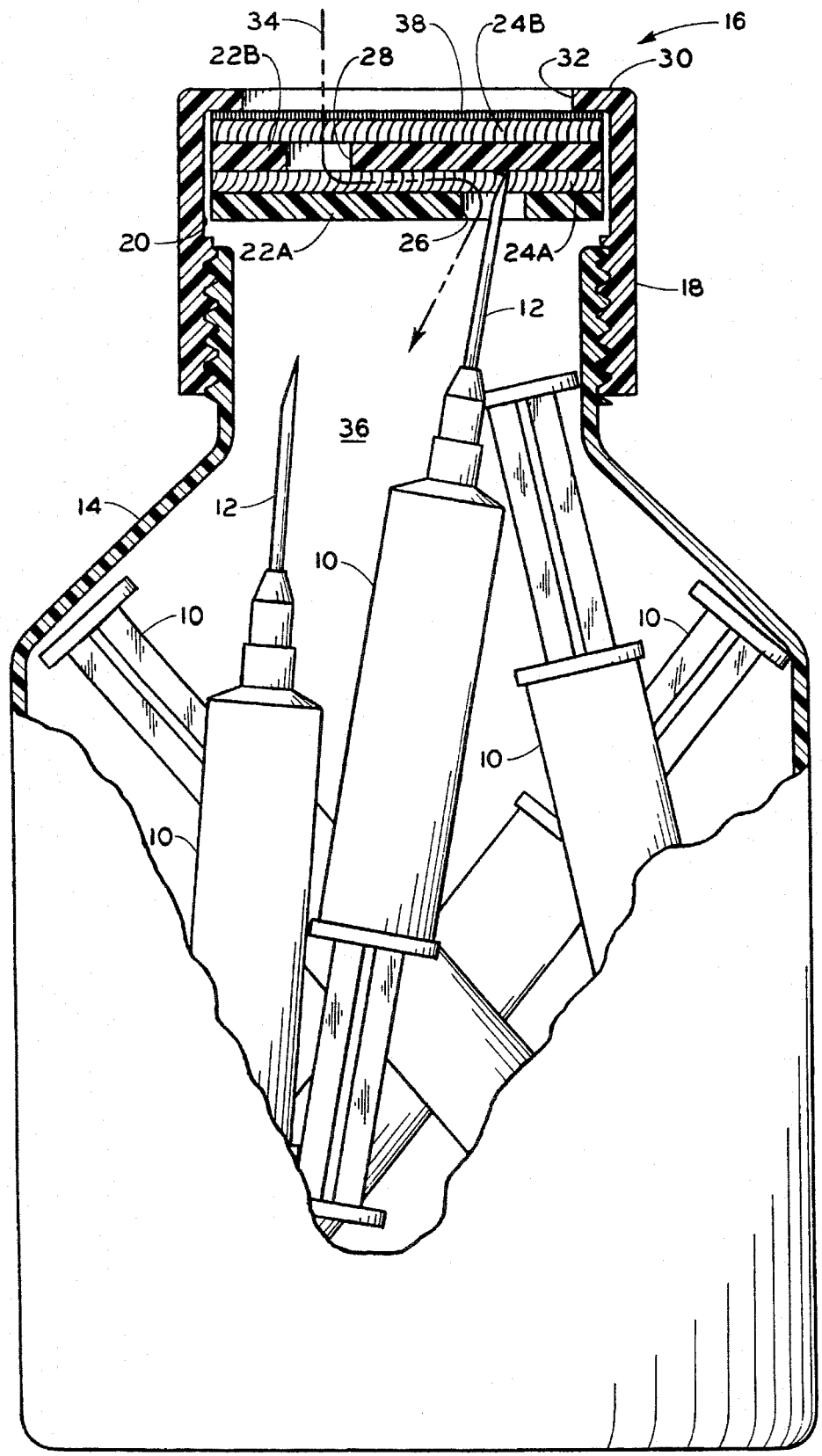
FIG. 1 is a longitudinal cross-sectional view of a hazardous material container, as typically used for a used disposable syringe with a needle as shown in this figure, and the within inventive autoclavable cap serving as a closure for the container.

As understood, hospitals as a most typical example, must abide by stringent requirements in the disposal of materials used on patients, which in hospital parlance is often referred to as "hazardous waste", in order to prevent, as an example, the transmittal of virus infections, such as the HIV virus resulting in AIDS, particularly if the hazardous waste is a used syringe needle. Thus, preparatory to the disposal of hazardous waste, and as illustrated in FIG. 1, a disposable syringe 10 with its needle 12 intact is typically accumulated in a container 14 having a screw cap, generally designated 16, serving as a closure for the container 14.

According to well understood requirements of waste disposal, the syringe needle 12 in its condition after use and as placed for accumulation in the container 14 is of an infectious nature requiring disposal in an incinerator. If autoclaved, however, the syringe needle 12 would qualify as non-infectious waste and can be legally disposed of in a land fill or, in hospital parlance, in a "clean fill", the cost or expense of using the latter being significantly less than that of the former, and also more environmentally preferred.

In accordance with the present invention, use is made of a construction for the cap 16 which is amenable to autoclaving of the syringe needles 12 while they are being accumulated in the container 14, while also maintaining safe conditions for storing the needles incident to their removal from the hospital environment.

Figure 2:
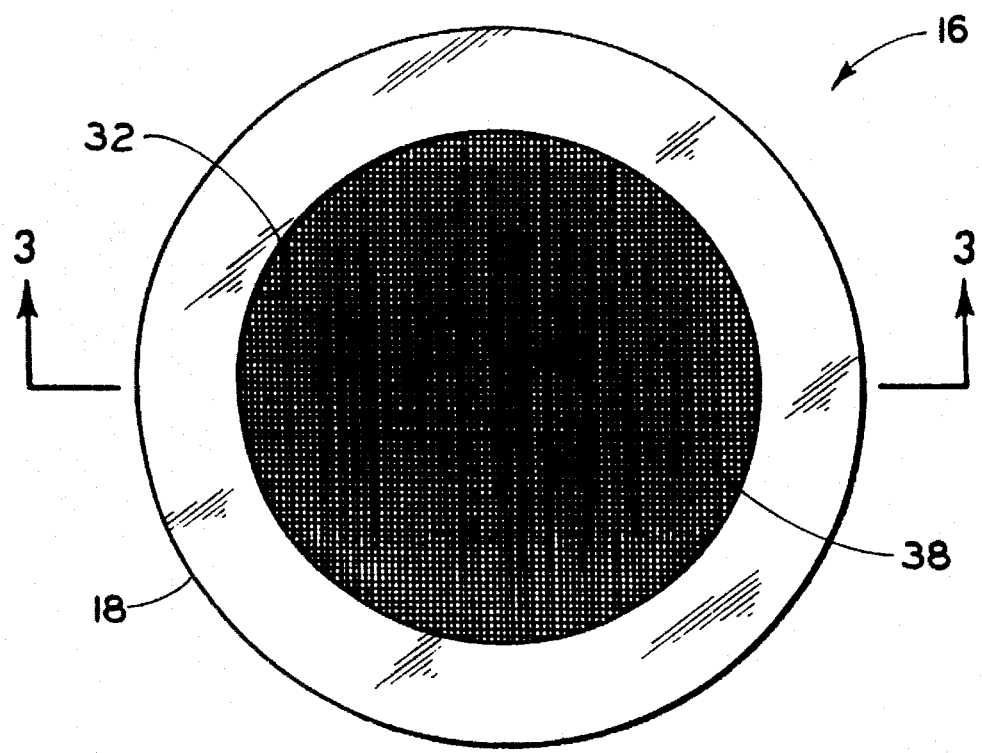
FIG. 2 is an isolated plan view of the cap.
Figure 3:
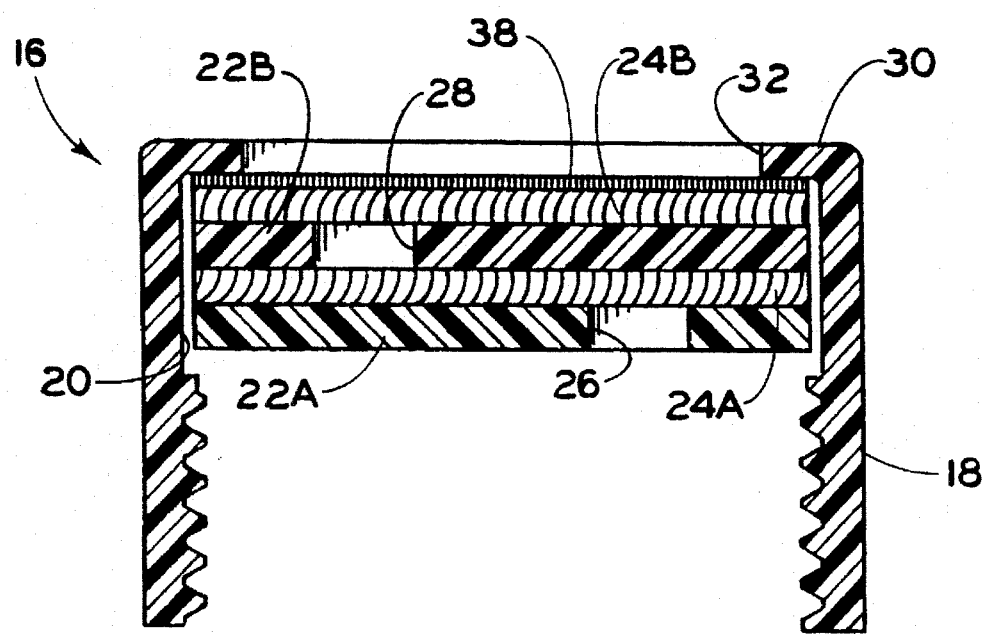
FIG. 3 is a side elevational view of the cap as taken along line 3—3 of FIG. 2.

As may best be understood from FIGS. 2 and 3 in conjunction with FIG. 1, cap 16 includes a cylindrical side wall 18 of a selected diameter and, conforming in shape to the cap and sized to be positioned within the compartment 20 bounded by the side wall 18 are at least four circular discs in alternating superposed relation, two of the discs designated 22A and 22B being of non-needle puncturable construction material such as a very rigid plastic, and the remaining two discs designated 24A and 24B being of steam permeable construction material. More particularly, discs 24A and 24B are, in a preferred embodiment, made of a needle-puncturable and thus less rigid plastic than that used for the discs 22A and 22B, but is a plastic which is wet heat sterilizable or autoclavable. By way of example, and as disclosed in U.S. Pat. No. 3,326,401 issued to DeLong et al. on Jun. 20, 1967, one such plastic is polypropylene. Polypropylene is a plastic which is capable of withstanding the high temperatures of an autoclave. An autoclave is an airtight chamber that can be filled with steam under pressure or surrounded by another chamber for the steam and that is used for sterilizing in moist or dry temperatures above 212 degrees F. without boiling.

Essential to the embodiment of the discs 22A and 22B are steam passage openings 26 and 28 and, just as essential, the non-aligning relation of the openings 26 and 28 to each other in their alternating relation beneath the top 30 of the cap 16 as positioned in the compartment 20. As a result, disc 22A is the first encountered in the superposed arrangement by a stored syringe needle 12 and the point of contact could be at the passageway opening 26. The needle 12 projects through the opening 26 and can also be expected to project through the less rigid autoclavable next encountered disc 24A, as shown in FIG. 1. However, next encountered by the needle 12 is the disc 22B which cannot be penetrated and, since the steam passage opening 28 thereof is not in the line of the exiting movement of the needle 12, disc 22B effectively prevents further penetration of needle 12 from the container 14. Stated otherwise, the first possibly encountered opening 26 confines the needle 12 to a movement path that cannot include the opening 28 since the openings 26 and 28 are not in alignment with each other. In this manner, the accumulated syringe needles 12, and other hazardous waste, are maintained under safe storage conditions.

To convert the infectious needles 12 to non-infectious waste to facilitate the disposal thereof, the closed container 14 is subjected, in a well understood manner, to sterilizing of its contents by steam autoclaving. To this end, the cap top 30 has a central opening 32 allowing steam to flow along the path 34 into the storage compartment 36 of the container 14.

Optional use can be made of a metal screen-like disc 38 beneath the hole 32 to minimize damage to the top disc 24B.

While the cap herein shown and disclosed in detail is fully capable of attaining the objects and providing the advantages hereinbefore stated, it is to be understood that it is merely illustrative of the presently preferred embodiment of the invention and that no limitations are intended to the detail of construction or design herein shown other than as defined in the appended claims.

What is claimed is:

1. A container cap for safe storage of syringe needles sterilized by steam autoclaving preparatory to a disposal thereof, said container cap comprising a cylindrical body having a top and internal threads on said body for threadable engagement to cooperating threads of a syringe needle-storing container, a superposed arrangement of discs of selected construction material disposed within said cap cylindrical body beneath said top thereof, at least a first and a second of said discs being of steam permeable construction material and at least a third and a fourth of said discs being of non-needle puncturable construction material, said first, second, third and fourth discs being in alternating relation in said superposed arrangement and said third and fourth discs having steam passage openings therein characterized by said opening being in a non-aligning relation to each other, whereby autoclaving steam flows externally into said syringe needle-storing container through said first and second discs and said third and fourth disc steam passage openings and any one of the stored syringe needles projecting through the steam passage opening of a first encountered one of said third and fourth discs is blocked from further projection by the next encountered other of said third and fourth discs as a result of said nonaligning relation of said third and fourth disc steam passage openings.

2. A container cap for safe storage of sharp-pointed articles sterilized by steam autoclaving preparatory to a disposal thereof, said container cap comprising a cylindrical body having a top and internal threads on said body for threadable engagement to cooperating threads of a storage container for sharp-pointed articles, a superposed arrangement of discs of selected construction material disposed within said cap cylindrical body beneath said top thereof, at least a first and a second of said discs being of steam permeable construction material and at least a third and a fourth of said discs being of impenetrable construction material, said first, second, third and fourth discs being in alternating relation in said superposed arrangement and said third and fourth discs having steam passage openings therein characterized by said opening being in a non-aligning relation to each other, whereby autoclaving steam flows externally into said storage container through said first and second discs and said third and fourth disc steam passage openings and any one of the stored sharp-pointed articles projecting through the steam passage opening of a first encountered one of said third and fourth discs is blocked from further projection by the next encountered other of said third and fourth discs as a result of said nonaligning relation of said third and fourth disc steam passage openings.

* * * * *